United States Patent [19]

Bryan et al.

[11] Patent Number: 5,385,896
[45] Date of Patent: Jan. 31, 1995

[54] BIOCIDAL COMPOSITIONS AND TREATMENTS

[75] Inventors: Edward Bryan, Stourbridge; Malcolm A. Veale, Redditch; Robert E. Talbot, Cannock; Kenneth G. Cooper, Hagley; Nigel S. Matthews, Horfield, all of England

[73] Assignee: Albright & Wilson Limited, Warley, England

[21] Appl. No.: 240,100

[22] Filed: May 9, 1994

Related U.S. Application Data

[63] Continuation of Ser. No. 985,362, Dec. 2, 1992, abandoned, which is a continuation of Ser. No. 863,465, Apr. 1, 1992, abandoned, which is a continuation of Ser. No. 711,356, Jun. 4, 1991, abandoned, which is a continuation of Ser. No. 486,787, Mar. 1, 1990, abandoned.

[30] Foreign Application Priority Data

Mar. 3, 1989 [GB] United Kingdom ............... 8904844

[51] Int. Cl.6 .................... A01N 35/02; A01N 57/00
[52] U.S. Cl. ...................... 514/129; 514/694
[58] Field of Search ................. 514/129, 694

[56] References Cited

U.S. PATENT DOCUMENTS 4,479,820 10/1984 Merk et al. ............................ 71/67
4,675,327 6/1987 Fredrich ............................ 514/383

FOREIGN PATENT DOCUMENTS

| | | |
|---|---|---|
| 2145708 | 4/1985 | United Kingdom . |
| 2178960 | 2/1987 | United Kingdom . |
| 2182563 | 5/1987 | United Kingdom . |
| 2201592 | 9/1988 | United Kingdom . |
| 2205310 | 12/1988 | United Kingdom . |
| 2228679 | 9/1990 | United Kingdom . |

*Primary Examiner*—Allen J. Robinson
*Attorney, Agent, or Firm*—Frishauf, Holtz, Goodman & Woodward

[57] ABSTRACT

Phosphonium salts such as THP and aldehydes such as formaldehyde exhibit synergistic biocidal activity.

14 Claims, No Drawings

BIOCIDAL COMPOSITIONS AND TREATMENTS

This application is a continuation of application Ser. No. 07/985,362 filed Dec. 2, 1992 (abandoned); which is a continuation of application Ser. No. 07/863,465 filed Apr. 1, 1992 (abandoned); which is a continuation of application Ser. No. 07/711,356 filed Jun. 4, 1991 (abandoned); which is a continuation of application Ser. No. 07/486,787 filed Mar. 1, 1990 (abandoned).

The present invention relates to biocidal compositions comprising tetraorgano phosphonium salts and biocidal treatments therewith.

Tetrakis hydroxymethyl phosphonium (herein referred to as "THP") salts and tris hydroxymethyl phosphine are described and claimed for use as biocides for water treatment, plant protection, and for pharmaceutical and veterinary treatments in GB 2145708, GB-A-2178960, GB-A-2182563, GB-A-2201592 and GB-A-2205310 the disclosures of which are hereby incorporated by reference. The use as biocides of certain analogues of THP, including the methyl, ethyl and allyl tris (hydroxymethyl) phosphonium salts, is described and claimed in British Application No. 9001831.8.

The low molecular weight phosphonium salts described in the aforesaid patents are quite distinct from the higher molecular weight quaternary surfactants which also exhibit biocidal properties. The quaternary surfactants differ markedly from the low molecular weight hydroxy methyl phosphonium biocides in their chemical, physical and biocidal properties. Thus both quaternary ammonium and quaternary phosphonium salts having one long (i.e. 8 to 20 carbon) chain are effective as biocides. The activity correlates with the surfactancy, declining as the length of the chain is reduced to 8 carbons. The quaternary ammonium salts, which are more effective as surfactants than the corresponding phosphonium salts are similarly more effective biocides.

The typical quaternary biocide has one fatty alkyl group and three methyl groups, but in the case of phosphonium salts the methyl groups can be substituted by hydroxymethyl groups without substantially affecting the biocidal activity. They may also be substituted by at least one aryl group e.g. the benzalkonium salts, without loss of either surfactancy or biocidal activity.

In contrast, the low molecular weight hydroxymethyl phosphonium salts are not surfactants and yet are highly active biocidally. The pattern of biocidal activity is quite different, however. They are effective against bacteria and algae at very much lower concentrations than the quaternary surfactants and are very rapid acting. Unlike the surfactants the activity of the low mol wt. phosphonium salts is specific to the presence of hydroxy methyl groups. Although it is possible to substitute one hydroxy methyl group by a methyl, ethyl or allyl group, without losing activity, if more than one hydroxy methyl group is substituted, or if the size of the substituent is increased above 3 carbon atoms the biocidal activity falls sharply. The tetra methyl phosphonium salts, and the aryl tris(hydroxymethy) phosphonium salts are inactive.

There is no nitrogen analogue to the low molecular weight phosphonium biocides.

For all the foregoing reasons THP salts and the related low molecular weight hydroxy methyl phosphonium and hydroxy methyl phosphine biocides are seen by those skilled in this art to form a quite distinct group of biocides in no way analogous to quaternary surfactants and presumably working by an entirely different mechanism. The use of long chain alkyl phosphonium salts for water treatment is known from EP066544.

A variety of aldehydes, such as formaldehyde, acrolein and glutaraldehyde are widely used as biocides. It is known that certain aldehydes are synergistic with quaternary surfactants.

We have now found that combinations of tris hydroxy methyl phosphine, or low molecular weight hydroxy methyl phosphonium biocides, especially THP salts, with aldehyde biocides, especially formaldehyde, and also glutaraldehyde and acrolein, possess synergistic biocidal properties.

The present invention provides biocidal compositions comprising (i) at least one organophosphorus biocide, which has the fomula

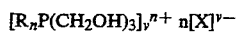

$$[R_nP(CH_2OH)_3]_v{}^{n+} \, n[X]^{v-}$$

wherein R is hydroxymethyl, methyl, ethyl or allyl, X is an anion such that the compound is at least sparingly soluble in water, n is 1 or 0 and v is the valency of the anion X and (ii) at least one biocidal aldehyde or polymer thereof.

The invention also provides a method of killing, or inhibiting the growth or reproduction of microbes or other pests on or in a substrate or medium, which comprises contacting said substrate or medium substantially simultaneously with the compounds (i) and (ii) specified above.

The preferred compounds for use are the THP salts, especially THP sulphate (THPS) and THP chloride (THPC), and tris(hydroxymethyl)phosphine.

Also useful are methyl tris(hydroxymethyl)phosphonium salts, ethyl tris(hydroxymethyl)phosphonium salts and allyl tris(hydroxymethyl)phosphonium salts.

The anion X may be any convenient anion which provides a salt which is preferably soluble at least to a concentration of 0.5 gm per liter of water at 25° C. such as chloride, sulphate or phosphate or less preferably sulphite, phosphite, bromide, nitrate, borate, acetate, formate, lactate, methosulphate, citrate or carbonate. However other anions may be used which provide salts of reduced solubility in water but are soluble in organic solvents e.g. alcohols or hydrocarbons.

The other key ingredient in our synergistic compositions is a biocidal aldehyde or biocidally active polymer thereof, such as formaldehyde, acetaldehyde, propionaldehyde, butyraldehyde, succinaldehyde, isobutyraldehyde, glutaraldehyde, crotonaldehyde, acrolein, chloral, glyoxal, metaldehyde, paraldehyde, metaformaldehyde or trioxan.

The phosphonium compound and the aldehyde may normally be present in the composition in a weight ratio of 20:1 to 1:20 especially 9:1 to 1:9 preferably 3:7 to 7:3.

It will be understood that THPC and THPS solutions as prepared usually contain a small amount of adventitious formaldehyde, typically about 2% or 3% by weight based on the THP salt, which is usually stripped down to under 1% before the product is supplied for use. It will be understood that the composition claims of the present invention do not refer to adventitious formaldehyde, but to formaldehyde added to the composition in addition to the trace that is normally present, to obtain synergistically enhanced biocidal action.

The biocidal components of our invention are useful for treating aerobic or anaerobic water systems contaminated or liable to be contaminated with microorganisms. For example they are effective against *Pseudomonas aeruginosa* and *Legionella pneumophila* in boiler water, cooling water, industrial process water, geothermal water, central heating and air conditioning systems, for killing algae in swimming pools, lakes, streams, canals and reservoirs and for treating cooling water in power stations and for marine engines.

The biocides are also useful in killing sulphate reducing bacteria such as Desulphovibrio in the above systems, and especially in oil field produced water, injection water, drilling fluids or water for hydrostatic testing. They are also useful as preservatives in aqueous based formulations such as bitumen and tar emulsions, paper sizes, adhesives, paints, cellulosic pulps including pulp thin stock and backwash recirculating liquor.

The biocides are useful in disinfectants including farmyard, domestic and surgical disinfectants. They may be used in the fumigation of grain silos, crops and crop storage areas.

The biocides are useful for killing bryophites, including mosses and liverworts, lichens, and sessile algae in lawns and gardens and on paths, drives, roadways, walls and other structures and on railways, airports and industrial estates.

The biocides are useful for protecting plants against fungi, bacteria, viruses and other microbial plant pathogens, by application to the plants and or to the soil in which they are growing or to be grown, or for use in a seed dressing.

The biocides may be used at higher concentrations as total herbicides, to kill higher plants.

The selective activity of the biocides is concentration dependent. Generally at concentrations of between 10 and 2,000 ppm preferably 20 to 1,500 e.g. 30 to 1,000 especially 50 to 500 ppm the biocides show selective activity against lower organisms such as bacteria, algae, mosses and fungi, but exhibit very low toxicity towards higher plants, fish and mammals. At higher concentrations, e.g. greater than 0.2% up to saturation, preferably 0.5 to 75% e.g. 1 to 60% and at dosages of greater than about 2 kg per hectare e.g. 2.5 to 5 kg per hectare the biocides are, however, effective total herbicides.

Mixed alkyl hydroxyalkyl THP salts may be prepared by adding an aqueous base to a tetrakis (hydroxymethyl) phosphonium salt, e.g. sodium hydroxide in a proportion of from 0.5 to 0.75 equivalents, to form tris (hydroxymethyl) phosphine and reacting the latter with alkyl halide such as methylchloride, preferably at an elevated temperature of e.g. 40°-60° C. Alternatively, improved yields may be obtained by reacting the alkylhalide with tris (acetoxymethyl) phosphine prepared by the method of Mironova et al, Zhur Obshch, Khim. 37, No 12, pages 2747-2752. The reaction may be carried out by heating at temperatures up to 140°, e.g. 120° C. in a suitable solvent such as toluene, for 2 to 20 hours e.g. 10 to 15 hours or with an acid catalyst, preferably acetic acid, for from 1 to 8 hours, e.g. 3 to 5 hours.

The invention provides compositions containing the aforesaid biocides. In particular for use in water treatment and in agriculture we have found that the biocides are synergistic with surfactants.

The surfactant may for example consist substantially of an at least sparingly water-soluble salt of sulphonic or mono esterified sulphuric acids, e.g. an alkylbenzene sulphonate, alkyl sulphate, alkyl ether sulphate, olefin sulphonate, alkane sulphonate, alkylphenol sulphate, alkylphenol ether sulphate, alkylethanolamide sulphate, alkylethanolamide ether sulphate, or alpha sulpho fatty acid or its esters each having at least one alkyl or alkenyl group with from 8 to 22, more usually 10 to 20, aliphatic carbon atoms.

The expression "ether" hereinbefore refers to compounds containing one or more glyceryl groups and/or an oxyalkylene or polyoxyalkylene group especially a group containing from 1 to 20 oxyethylene and/or oxypropylene groups. One or more oxybutylene groups may additionally or alternatively be present. For example, the sulphonated or sulphated surfactant may be sodium dodecyl benzene sulphonate, potassium hexadecyl benzene sulphonate, sodium dodecyl dimethyl benzene sulphonate, sodium lauryl sulphate, sodium tallow sulphate, potassium oleyl sulphate, ammonium lauryl monoethoxy sulphate, or monoethanolamine cetyl 10 mole ethoxylate sulphate.

Other anionic surfactants useful according to the present invention include alkyl sulphosuccinates, such as sodium di-2-ethylhexylsulphosuccinate and sodium dihexylsulphosuccinate, alkyl ether sulphosuccinates, alkyl sulphosuccinamates, alkyl ether sulphosuccinamates, acyl sarcosinates, acyl taurides, isethionates, soaps such as stearates, palmitates, resinates, oleates, linoleates, and alkyl ether carboxylates. Anionic phosphate esters and alkyl phosphonates, alkyl amino and imino methylene phosphonates may also be used. In each case the anionic surfactant typically contains at least one aliphatic hydrocarbon chain having from 8 to 22, preferably 10 to 20 carbon atoms, and, in the case of ethers, one or more glyceryl and/or from 1 to 20 oxyethylene and/or oxypropylene and/or oxybutylene groups.

Preferred anionic surfactants are sodium salts. Other salts of commercial interest include those of potassium, lithium, calcium, magnesium, ammonium, monoethanolamine, diethanolamine, triethanolamine, alkyl amines containing up to seven aliphatic carbon atoms, and alkyl and/or hydroxyalkyl phosphonium.

The surfactant may optionally contain or consist of nonionic surfactants. The nonionic surfactant may be, e.g. a $C_{10-22}$ alkanolamide of a mono or di-lower alkanolamine, such as coconut monoethanolamide. Other nonionic surfactants which may optionally be present, include tertiary acetylenic glycols, polyethoxylated alcohols, polyethoxylated mercaptans, polyethoxylated carboxylic acids, polyethoxylated amines, polyethoxylated alkylolamides, polyethoxylated alkylphenols, polyethoxylated glyceryl esters, polyethoxylated sorbitan esters, polyethoxylated phosphate esters, and the propoxylated or ethoxylated and propoxylated analogues of all the aforesaid ethoxylated nonionics, all having a $C_{8-22}$ alkyl or alkenyl group and up to 20 ethyleneoxy and/or propyleneoxy groups. Also included are polyoxypropylene/polyoxethylene copolymers, polyoxybutylene/polyoxyethylene copolymers and polyoxybutylene/polyoxypropylene copolymers. The polyoxyethylene polyoxypropylene and polyoxybutylene compounds may optionally be end-capped with, e.g. benzyl groups to reduce their foaming tendency.

Compositions of our invention may contain an amphoteric surfactant.

The amphoteric surfactant may for example be a betaine, e.g. a betaine of the formula: $-R_3N^+CH_2COO^-$, wherein each R is an alkyl, cycloalkyl, alkenyl or alkaryl group and preferably at least one, and most preferably not more than one R, has an average of from 8 to 20, e.g. 10 to 18 aliphatic carbon atoms and each other R has an average of from 1 to 4 carbon atoms. Particularly preferred are the quaternary imidazoline betaines of the formula:

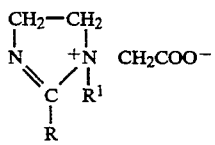

wherein R and $R^1$ are alkly, alkenyl, cycloalkyl, alkaryl or alkanol groups having an average of from 1 to 20 aliphatic carbon atoms and R preferably has an average of from 8 to 20, e.g. 10 to 18 aliphatic carbon atoms and $R^1$ preferably has 1 to 4 carbon atoms. Other amphoteric surfactants for use according to our invention include alkyl amine ether sulphates, sulphobetaines and other quaternary amine or quaternised imidazoline sulphonic acids and their salts, and other quaternary amine or quaternised imidazoline carboxylic acids and their salts and Zwitterionic surfactants, e.g. N-alkyl taurines, carboxylated amido amines such as $RCONH(CH_2)_2N^+ (CH_2CH_2CH_3)_2CH_2CO_2$, and amino acids having, in each case, hydrocarbon groups capable of conferring surfactant properties (e.g. alkyl, cycloalkyl, alkenyl or alkaryl groups having from 8 to 20 aliphatic carbon atoms).

Typical examples include 2 tallow alkyl, 1-tallow amido alkyl, 1-carboxymethyl imidazoline and 2 coconut alkyl N-carboxymethyl 2-(hydroxyalkyl) imidazoline. Generally speaking any water soluble amphoteric or Zwitterionic surfactant compound which comprises a hydrophobic portion including a $C_{8-20}$ alkyl or alkenyl group and a hydrophilic portion containing an amine or quaternary ammonium group and a carboxylate, sulphate or sulphonic acid group may be used in our invention.

Compositions of our invention may also include cationic surfactants.

The cationic surfactant may for example be an alkylammonium salt having a total of at least 8, usually 10 to 30, e.g. 12 to 24 aliphatic carbon atoms, especially a tri or tetra-alkylammonium salt. Typically alkylammonium surfactants for use according to our invention have one or at most two relatively long aliphatic chains per molecule (e.g. chains having an average of 8 to 20 carbon atoms each, usually 12 to 18 carbon atoms) and two or three relatively short chain alkyl groups having 1 to 4 carbon atoms each, e.g. methyl or ethyl groups, preferably methyl groups.

Typical examples include dodecyl trimethyl ammonium salts. Benzalkonium salts having one 8 to 20 C alkyl group two 1 to 4 carbon alkyl groups and a benzyl group are also useful.

Another class of cationic surfactants useful according to our invention are N-alkyl pyridinium salts wherein the alkyl group has an average of from 8 to 22, preferably 10 to 20 carbon atoms. Other similarly alkylated heterocyclic salts, such as N-alkyl isoquinolinium salts, may also be used.

Alkylaryl dialkylammonium salts, having an average of from 10 to 30 aliphatic carbon atoms are useful, e.g. those in which the alkylaryl group is an alkyl benzene group having an average of from 8 to 22, preferably 10 to 20 aliphatic carbon atoms and the other two alkyl groups usually have from 1 to 4 carbon atoms, e.g. methyl groups.

Other classes of cationic surfactant which are of use in our invention include alkyl imidazoline or quaternised imidazoline salts having at least one alkyl group in the molecule with an average of from 8 to 22 preferably 10 to 20 carbon atoms. Typical examples include alkyl methyl hydroxyethyl imidazolinium salts, alkyl benzyl hydroxyethyl imidazolinium salts, and 2 alkyl-1-alkylamidoethyl imidazoline salts.

Another class of cationic surfactant for use according to our invention comprises the amido amines such as those formed by reacting a fatty acid having 8 to 22 carbon atoms or an ester, glyceride or similar amide forming derivative thereof, with a di or poly amine, such as, for example, ethylene diamine or diethylene triamine, in such a proportion as to leave at least one free amine group. Quaternised amido amines may similarly be employed.

Alkyl phosphonium and hydroxyalkyl phosphonium salts having one $C_{8-20}$ alkyl groups and three $C_{1-4}$ alkyl or hydroxyalkyl groups may also be used as cationic surfactants in our invention.

Typically the cationic surfactant may be any water soluble compound having a positively ionised group, usually comprising a nitrogen atom, and either one or two alkyl groups each having an average of from 8 to 22 carbon atoms.

The anionic portion of the cationic surfactant may be any anion which confers water solubility, such as formate, acetate, lactate, tartrate, citrate, chloride, nitrate, sulphate or an alkylsulphate ion having up to 4 carbon atoms such as a methosulphate. It is preferably not a surface active anion such as a higher alkyl sulphate or organic sulphonate.

Polyfluorinated anionic, nonionic or cationic surfactants may also be useful in the compositions of our invention. Examples of such surfactants are polyfluorinated alkyl sulphates and polyfluorinated quaternary ammonium compounds.

Compositions of our invention may contain a semi-polar surfactant, such as an amine oxide, e.g. an amine oxide containing one or two (preferably one) $C_{8-22}$ alkyl group, the remaining substituent or substituents being preferably lower alkyl groups, e.g. $C_{1-4}$ alkyl groups or benzyl groups.

Particularly preferred for use according to our invention are surfactants which are effective as wetting agents, typically such surfactants are effective at lowering the surface tension between water and a hydrophobic solid surface. We prefer surfactants which do not stabilise foams to a substantial extent.

Mixtures of two or more of the foregoing surfactants may be used. In particular mixtures of non-ionic surfactants with cationic and/or amphoteric and/or semi polar surfactants or with anionic surfactants may be used. Typically we avoid mixtures of anionic and cationic surfactants, which are often less mutually compatible.

Preferably the organo phosphorus compound and the surfactant are present in a relative weight concentration of from 1:1000 to 1000:1, more usually 1:50 to 200:1, typically 1:20 to 100:1, most preferably 1:10 to 50:1, e.g. 1:1 to 20:1 especially 2:1 to 15:1.

Effective doses of the mixture of organophosphorus compound, aldehyde and surfactant are typically from 2 ppm to 2000 ppm more usually 20 ppm to 1,000 ppm e.g. 50 ppm to 500 ppm especially 100 to 250 ppm.

Compositions for use in water treatment may additionally or alternatively contain other biocides, oxygen scavengers, dispersants, antifoams, solvents, scale inhibitors, corrosion inhibitors and/or flocculants.

Compositions according to our invention for use in controlling bryophites, lichens or fungal or microbial plant pathogens, contain an effective amount of a biocide as aforesaid, together with a horticulturally or agriculturally acceptable diluent, carrier and/or solvent therefor.

The organo phosphorus compounds may be present as a solution in water at effective concentrations up to saturation. They will usually be supplied as concentrates at about 50 to 80% by weight concentration, e.g. 75% by wt. before mixing with the aldehyde but will normally be diluted to a concentration of from 0.01 to 10% by wt. before application. Where damage to higher plants is to be avoided it is preferred to use concentrations below 1% w/w biocide, preferably below 0.2%. Alternatively the biocides may be admixed with or absorbed upon inert, particulate, non-phytotoxic solids such as talc or dissolved in organic solvents or suspended in or as dispersions or emulsions. Thus the compostions of the invention are preferably in the form of emulsifiable concentrates in organic solvents such as alcohols hydrocarbons, and amides such as dimethyl formamide including cyclic amides such as N-methyl pyrrolidone, the concentrate also containing a surfactant e.g. as specified above. They may be used in conjunction with other moss killers or biocides, such as herbicides, fungicides, bactericides, insecticides and weedkillers, or with surfactants, wetting agents, adhesives, emulsifiers, suspending agents, thickeners, synergists, hormones, plant growth regulators or plant nutrients.

The compositions of our invention may be applied to lawns, flower or vegetable beds, arable land, meadowland, orchards or woodland, or hydroponic beds, or to the seeds, roots, leaves, flowers, fruit and/or stems of plants, or to paths, roads, walls, wood-work, brickwork or similar invasible surfaces.

The composition may be of value, inter alia, in controlling moss or sessile algae in lawns or on paths or walls, as seed dressings, as sprays for controlling fungal, bacterial or viral infections on leaves, flowers and fruit, such as mildew, botrytis, rust, fusarium, mosaic diseases or wilt, for application to soil or to the roots of seedlings (e.g. of brassica seedlings to inhibit club root) and in the control of numerous fungal, vital, protozoal and bacterial diseases of plants, including fungal blights such as potatoe blight, cankers such as apple canker, scabs, root rot, and base rot of bulbs. The compositions are especially effective in protecting cereal crops including wheat, barley, rye, oats, rice maize millet and sesame against a broad spectrum of plant diseases.

Other crops of importance which may be protected according to our invention include sugar cane; root vegetables including carrots, parsnips, turnips, beetroot, sugar beet, radishes, swedes and mangolds; brassicas including cabbages, broccoli, cauliflower and sprouts; grazing land; pulses including peas, broad beans, French, beans, runner beans, navy beans, kidney beans and lentils; curcubaceous plants including cucumbers, marrows, gourds and squashes, oilseed rape, timber, rubber, cotton, coffee, cocoa, jute, tomatoes, potatoes, yams, tobacco, bananas, coconut palm, olives, alliums including onions, shalots, leeks, garlic, chives and spring onions, ground nuts, peanuts, sorghum, oil palm, roses, hemp, flax, lucerne, alfalfa, tea and fruit, including citrus fruit, apples, plums, peaches, nectarines, mangoes, pears, cherries, grapes, berries, currants, dates, figs, avocados, almonds, and apricots.

The mixtures of tetra organophosphonium compounds and aldehydes are more effective biocides, against a variety of microorganisms and pests, than the individual compounds. In the case of formaldehyde the formulation may be prepared substantially in advance and stored prior to use. In the case of certain of the other aldehydes however, it is preferred to prepare the composition in situ by adding the aldehyde and the organophosphonium biocide separately to the locus to be treated or to mix them as required for use, since the two compounds are chemically incompatible, if mixed together and stored for long periods.

The invention is illustrated in the following Examples THPS means bis [tetrakis(hydroxymethyl) phosphonium] sulphate. "Empigen" is a registered trademark of Albright & Wilson Limited. "Empigen" BAC is a fatty alkyl dimethyl benzyl ammonium chloride.

EXAMPLE

1. METHOD 1.1 Biofilm generation

Mild steel biostuds were allowed to foul over a 3 week period with a mixed microbiological enrichment of sulphate-reducing bacteria (SRB), aerobic bacteria and anaerobic bacteria from North Seal oil production platform water injection systems. This was accomplished using a recirculating biofilm generator specially designed for the purpose. The device was constructed of PVC pipe, containing a row of mild steel studs, mounted so that their exposed faces were flush with the interior of the pipe. The culture medium was circulated by means of a centrifugal pump and any gas build up was removed from the system using a bleed valve. Sterile anaerobi fresh nutrient/seawater medium was bled into the system daily to maintain the growth of the biofilm; 75% of the fluid volume of the device being replaced each day. The device was run for 3 weeks to allow a table biofilm to develop. Check studs were removed regularly to confirm the stability of biofilm build up.

1.2 Biocide test regimes

The biocides tested were are follows:

| BIOCIDE | COMPONENT | WEIGHT FRN | % ACTIVE w/w |
|---|---|---|---|
| 1 | THPS | 0.1551 | 11.63 |
|  | Empigen BAC | 0.0233 | 1.17 |
|  | 36.6% Formaldehyde | 0.2869 | 10.50 |
|  | Water | 0.5347 |  |
|  | Total actives |  | 23.30 |
| 2 | THPS | 0.2951 | 22.13 |
|  | Empigen BAC | 0.0233 | 1.17 |
|  | Water | 0.6816 |  |
|  | Total actives |  | 23.30 |
| 3 | 36.6% Formaldehyde | 0.6323 | 22.13 |
|  | Empigen BAC | 0.0233 | 1.17 |
|  | Water | 0.3444 |  |
|  | Total actives |  | 23.30 |

The three products were challenged against sessile populations using the standard static method text described in section 1.3. This test is designed to determine the concentration necessary to kill aerobi, anaerobic and SRB bacteria after a contact time of one hour.

1.3 Static biocide tests

Individual fouled studs were suspended in separate 125 ml vessels containing seawater/biocide solution at the appropriate concentration. The biocide solutions were prepared using sterile., anaerobi seawater and required concentrations of biocide.

1.4 Enumeration of bacteria

After one hour of exposure, the studs were removed to 10 ml volumes of anaerobic diluent containing 1 g of sand. Vortex mixing was used to disrupt the biofilm and produce a homogenous suspension. The initial dilution was then serially diluted to $10^{-8}$ in further 10 ml aliquots of anaerobic diluent. Control studs, exposed to seawater without biocide, were treated in an identical manner to ensure comparability with the biocide treated studs.

The dilution series were then used to inoculate selective enumeration media: lactate based broth media for enumeration of SRB; anaerobic seawater yeast/peptone agar (in an anaerobic cabinet) for anaerobi bacteria; seawater nutrient agar for aerobi bacteria. Enumeration series were incubated at 30° C. Aerobic and anaerobi bacteria were counted after 5 days incubation and SRB numbers were determined after a full incubation period of 28 days.

2. RESULTS

| Biocide | Conc (ppm) | Contact Time (hrs) | Surviving bacteria per stud | | |
|---|---|---|---|---|---|
| | | | SRB | Anaerobes | Aerobes |
| Control | 0 | 1 | $1.1 \times 10^5$ | $2.3 \times 10^5$ | $2.4 \times 10^5$ |
| | | 1 | $1.1 \times 10^5$ | $3.1 \times 10^5$ | $2.9 \times 10^5$ |
| | 100 | 1 | $2.5 \times 10^5$ | $2.9 \times 10^4$ | $1.0 \times 10^3$ |
| | 250 | 1 | $2.5 \times 10^1$ | $2.0 \times 10^4$ | 0 |
| 1 | 500 | 1 | 0 | $5.0 \times 10^2$ | 0 |
| | 1000 | 1 | 0 | 0 | 0 |
| | 1500 | 1 | 0 | 0 | 0 |
| | 100 | 1 | $4.5 \times 10^4$ | $8.5 \times 10^4$ | $3.5 \times 10^3$ |
| | 250 | 1 | $2.4 \times 10^1$ | $1.3 \times 10^4$ | 0 |
| 2 | 500 | 1 | 0 | $4.0 \times 10^3$ | $1.0 \times 10^2$ |
| | 1000 | 1 | 0 | $5.0. \times 10^2$ | 0 |
| | 1500 | 1 | 0 | 0 | 0 |
| | 100 | 1 | $4.5 \times 10^3$ | $3.0 \times 10^4$ | $1.8 \times 10^3$ |
| | 250 | 1 | $1.1 \times 10^5$ | $4.3 \times 10^4$ | $1.9 \times 10^3$ |
| 3 | 500 | 1 | $1.5 \times 10^6$ | $4.5 \times 10^5$ | $2.3 \times 10^4$ |
| | 1000 | 1 | $4.5 \times 10^4$ | $1.0 \times 10^4$ | $5.0 \times 10^2$ |
| | 1500 | 1 | $1.1 \times 10^3$ | $1.7 \times 10^4$ | $4.0 \times 10^2$ |

3. COMMENTS 3.1 The control levels of SRB, anaerobes and aerobes are all high indicating the presence of the high concentration of viable bacteria in the biofilms.

3.2 All biocides contain the same total active level.

3.3 The results for biocide 3 (Formaldehyde based) show that this system is not very effective.

3.4 The results for biocide 2 (THPS based) show it to be fairly active.

3.5 The results for biocide 1 (THPS/Formaldehyde based) show it to be more effective than biocide 2 despite having a lower THPS content (the deficit being made up with less active formaldehyde). It is therefore apparent that synergism is occurring.

EXAMPLE 2

A composition comprising equal proportions of a glutaraldehyde and THPS showed increased activity against bacteria compared with glutaraldehyde and increased activity against fungi compared with THPS at equivalent total biocide concentrations. In each case the activity was substantially greater than the mean of the activities of the separate biocides.

We claim:

1. A synergistic bactericide composition, said composition comprising effective synergistically active proportions of:
   (i) tetrakis hydroxymethyl phosphonium sulphate and
   (ii) formaldehyde,
wherein said tetrakis hydroxymethyl phosphonium sulphate and said formaldehyde are present in a relative weight proportion of from 20:1 to 1:20.

2. The composition according to claim 1 wherein (i) and (ii) are present in a relative weight proportion of from 9:1 to 1:9.

3. A method of killing or inhibiting the growth of bacteria, comprising applying to the bacteria, or to a locus thereof an antibacterial effective amount of the composition of claim 1 or forming said composition in situ by adding the tetrakis hydroxymethyl phosphonium sulfate and the formaldehyde separately during said applying wherein the in situ composition is in synergistic effective amounts.

4. The method according to claim 3 wherein the locus is water.

5. The method according to claim 4 wherein the water is industrial process water, boiler water, cooling water, water in central heating or air conditioning systems, geothermal water or water in swimming pools.

6. The method according to claim 3 wherein the locus is oil field produced water, injection water, drilling fluids or water for hydrostatic testing of pipelines.

7. The method according to claim 3 wherein the locus is paper mill thin stock or backwater.

8. The method according to claim 3 wherein the locus is a surface which is disinfected.

9. The method according to claim 3 wherein (i) and (ii) are present in a relative weight proportion of 3:7 to 7:3.

10. The method according to claim 3 wherein the bacteria are *Pseudomonas aeruginosa, Legionella pneumophia* or Desulphovibrio.

11. The method according to claim 3 wherein the composition is applied at a concentration of 10 to 2,000 ppm.

12. The method according to claim 3 wherein the composition is applied at a concentration of 20 to 1,500 ppm.

13. The method according to claim 3 wherein the composition is applied at a concentration of 30 to 1,000 ppm.

14. The method according to claim 3 wherein the composition is applied at a concentration of 50 to 500 ppm.

* * * * *